United States Patent
Dhar et al.

(10) Patent No.: US 9,889,105 B2
(45) Date of Patent: Feb. 13, 2018

(54) IN VIVO METHOD FOR TREATING, INHIBITING, AND/OR PROPHYLAXIS OF CANCER, SUCH AS PANCREATIC CANCER

(71) Applicants: Animesh Dhar, Fairway, KS (US); William G. Gutheil, Kansas City, MO (US)

(72) Inventors: Animesh Dhar, Fairway, KS (US); William G. Gutheil, Kansas City, MO (US)

(73) Assignees: U.S. Department of Veterans Affairs, Washington, DC (US); Univ. of Kansas, Lawrence, KS (US); The Curators of the Univ. of Missouri, Columbia, MO (US)

( * ) Notice: Subject to any disclaimer, the term of this patent is extended or adjusted under 35 U.S.C. 154(b) by 0 days.

(21) Appl. No.: 14/246,305

(22) Filed: Apr. 7, 2014

(65) Prior Publication Data

US 2014/0221491 A1 Aug. 7, 2014

Related U.S. Application Data

(63) Continuation-in-part of application No. 13/883,061, filed as application No. PCT/US2011/001735 on Oct. 7, 2011.

(60) Provisional application No. 61/344,879, filed on Nov. 2, 2010.

(51) Int. Cl.
*A61K 31/194* (2006.01)
*A61K 31/202* (2006.01)

(52) U.S. Cl.
CPC .................. *A61K 31/202* (2013.01)

(58) Field of Classification Search
CPC ...................................... A61K 31/202
USPC .......................... 514/574; 435/375
See application file for complete search history.

(56) References Cited

U.S. PATENT DOCUMENTS

| | | |
|---|---|---|
| 2006/0194973 A1 | 8/2006 | Gainer et al. |
| 2006/0276372 A1 | 12/2006 | Lockwood et al. |
| 2010/0210572 A1 | 8/2010 | Eidenberger |
| 2013/0231300 A1 | 9/2013 | Dhar et al. |

OTHER PUBLICATIONS

Glossary of medical education terms, Institute of International Medical Education. http://www.iime.org/glossary.htm Accessed in Mar. 2013.*
Tanaka et al. Cancer Chemoprevention by Carotenoids. Molecules 17:3202-3242, 2012.*
Dhar et al. Crocetin inhibits pancreatic cancer cell proliferation and tumor progression in a xenograft mouse model. Mol Cancer Ther 8:315-323, 2009.*
Wei et al. Expression of CD44, CD24 and ESA in pancreatic adenocarcinoma cell lines varies with local microenvironment. Hepatobiliary Pancreat Dis Int 10:428-434, 2011.*
Bao et al. Pancreatic Cancer Stem-like Cells Display Aggressive Behavior Mediated via Activation of FoxQ1. J Biol Chem 289:14520-14533, 2014.*
Siegel, R., Naishadham, D and Jemal, A. Cancer Statistics 2013, CA Cancer J. Clin 63, 11-30, 2013.
Nair, SC, Panikkar B, Panikkar KR. Antitumor activity of saffron (*Crocus sativus*). Cancer Lett 1991; 57:109-14.
Abdullaev FI, Frenkel GD. Effect of saffron on cell colony formation and cellular nucleic acid and protein synthesis. Biofactors 1992; .3:201-04.
Abdullaev FI. Cancer chemopreventive and tumoricidal proporties of saffron (*Crocus sativus* L.) Exp. Biol. Med. 2002; 227: 20-5.
Abdullaev FI. Espinosa-Aguirre JJ. Biomedical properties of Saffron and its potential use in cancer therapy and chemoprevention trials. Cancer Detection and Prevention. 2004; 28, 426-32 (13 pages).
Tarantilis PA, Morjani H, Polissiou M, et al. Inhibition of growth and induction of differentiation of promyelocytic leukemia (HL-60) by carotenoids from *C. Sativus* L. Anticancer Res 1994;14:1913-18.
Dhar, A.; Mehta, S.; Dhar, G., Dhar, K.; Banerjee, S.; Van Veldhuizen,P.; Campbell, D.R.; Bannerjee, S.K. Crocetin inhibits pancreatic cancer cell proliferation and tumor progression in a xenograft mice model. *Mol. Cancer Ther.*, 2009, 8 315-323. Published Online First Feb. 10, 2009.
Gutheil, W., Reed, G., Ray, A., Anant, S. and Dhar, A. Crocetin: a novel agent derived from saffron from prevention and therapy for cancer. Current Pharmaceutical Biotechnology 13, 173-179, 2012.
Giaccio, M. Crocetin from Saffron: An active component of an ancient spice. *Clin. Rev. Food Sc. Nutr.*, 2004, 44, 155-172.
Sujata, V.; Ravishankar, G. A.; Venkataramn, L. V. Methods for the analysis of the saffron metabolites crocin, crocetins, picocrocin and safranal for the determination of the quality of the spice using thin layer chromatography, high performance liquid chromatography and gas chromatography. *J. Chromatogr.*, 1992, 624, 497-502.
Li, N.; Lin, G.; Kwan, Y-W.; Min, Z-D. Simultaneous quantification of five major biologically active ingredients of saffron by highperformance liquid chromatography. *J. Chromatogr.*, 1999, 849,349-355.
Abdullaev FI. Inhibitory effect of Crocetin on intracellular nucleic acid and protein synthesis in malignant cells. Toxicol Lett 1994; 70:243-51.
Nair SC, Kururumboor SK, Hasegawa JH Saffron chemoprevention in biology and medicine: a review. Cancer Biother 1995; 10:257-64.
Ashrafi M, Bathari SZ, Taghikhani M, et al.. The effect of carotenoids obtained from saffron from on histone H1 structure and H1-DNA interaction. Int J Biol Macromol 2005; 36:246-52.
Magesh, V.; Singh, J.P.; Selvendiran, K.; .Ekambaram, B.; Sakthisekaran, D. Antitumor activity of crocetin in accordance to tumor incidence, antioxidant status, drug metabolizing enzymes and histopathological studies. *Mol. Cell. Biochem.*, 2006, 287, 127-135.
Chryssanthi DG, Lamar FN, Iatrou G, et al.Inhibition of breast cancer cell proliferation by style constituents of different *Crocus* species. Anticancer Res 2007; 27, 357-62.

(Continued)

*Primary Examiner* — Yih-Horng Shiao
(74) *Attorney, Agent, or Firm* — Dinesh Agarwal, P.C.

(57) ABSTRACT

An in vivo method of inhibiting tumor growth, specifically pancreatic cancer, includes administering to a subject in need thereof an effective amount of a compound, composition, and/or a pharmaceutical formulation including crocetinic acid.

2 Claims, 8 Drawing Sheets
(5 of 8 Drawing Sheet(s) Filed in Color)

(56) References Cited

OTHER PUBLICATIONS

Dhar, A., Fogt, L., Subramaniam, D. and Anant, S. Cancer Stem Cells: Novel target using dietary components for prevention and treatment. Nutraceutical and Cancer ed Sarkar, F.S. P11-38, 2012 (Sep. 20, 2011) (31 pages).
Rosenberg L. Pancreatic Cancer: A review of Emerging Therapies. Drugs 59, 1071-1089, 2000.
Balasubramonian S, Chandraratna RA, Eckert, RL. A novel-retenoid related molecule inhibits pancreatic cell proliferation be a retinoid receptor independent mechanism via suppression of cell cycle regulatory protein function and induction of caspase-associated apoptosis. Oncogene 2005; 24:4257-70.
Mathews-Roth MM. Effect of crocetin on experimental skin tumors. Oncology 1982; 39, 362-64.
Lemoine NR, Hughes CM, Barton, C.M, et al. The epidermal growth factor receptor in human pancreatic cancer. J Pathol 1992; 166: 7-12.
Dhar A, Mehta S, Banerjee S, et al. Epidermal growth factor receptor, Is a novel therapeutic target for pancreatic cancer? Front Biosci 2005;10:1763-67 (7 pgs).
Yamanka Y, Freiss H, Korbin MS, et al. Coexpression of epidermal growth factor receptor and ligands in human pancreatic cancer associated with enhanced tumor aggressiveness. Anticancer Res 1993; 13:565-69.
Tsujimoto Y. Stress resistance conferred by high level of bcl-2 protein in human lyphoblastoid cell. Oncogene 1989; 4:1331-36.
Hawkins CJ, Vaux, D. Analysis of the role of bcl-2 in apoptosis. Immunol Rev 1994; 142: 127-39
Oltvai ZN, Milliman CL, Korsmeyer SJ. Bcl-2 hetrodimerizes in vivo with a conserved homolog, Bax, that acclerates program cell death. Cell 1993; 74: 609-19.
Yin XM, Oltvai, ZN, Korsmeyer SJ. BH1 and Bh2 domains of Bcl-2 are required for inhibition of apoptosis and hetrodimerization with Bax. Nature 1994; 369: 321-23.
Lapidot, T, Sirard, Sirard, C, Vormoor, J et al (1994) A cell initiating human acute myeloid leukemia after transplantation into SCID mice. Nature 367; 645-648.
Bonnet D, Dick JE. (1997)Human acute myeloid leukemia is organized as a hierarchy that originates from a primitive hematopoietic cell. Nat Med 3, 730-737.
Gupta, S, Hussain, T, Mukhtar, H (2003)Molecular pathway for (-)-epigallocatechin-3-gallate-induced cell cycle arrest and apoptosis of human prostate carcinoma cells. Arch Biochem Biophys 410, 177-185.
Korkaya H, Paulson A, Charafe-Jauffret E, et al (2009). Regulation of mammary stem/progenitor cells by PTEN/Akt/beta-catenin signaling. PLoS Biol e1000121, vol. 7 (14 pgs).
Liu S, Dontu G, Wicha MS (2005) Mammary stem cells, self-renewal pathways, and carcinogenesis. Breast Cancer Res 7, 86-95.
Zhou BB, Zhang H, Damelin M et al (2009) Tumour-initiating cells: challenges and opportunities for anticancer drug discovery. Nat Rev Drug Discov. 8, 806-823.
Mwangi, SM, Srinivasan, S (2010) DCAMKL-1: A new horizon for pancreatic progenitor identification (Comment). Am J Physiol Gastrointest Liver Physiol 299, G301-G302.
May, R, Sureban, SM, Lightfoot, SA et al (2010) Identification of a novel putative/pancreatic stem cell marker DCAMKL-1 in normal mouse pancreas. Am J Physiol Gastrointest Liver Physiol 299, G303-G310.
Cohen Jr MM. (2003) The hedgehog signaling network. Am J Med Genet 123A, 5-28.
Jemal, A., Siegel, R., Ward, E., Hao, Y., Xu, J. and Thun, M.J. Cancer Statistics, 2009. CA Cancer J. Clin 59, 225-249, 2009.
Chua, Y.J. and Zalcberg, J.R. Pancreatic Cancer—is the wall crumbling? Annals of Oncology 19, 1224-1230, 2008.
Rosenberg L, Lipsett M.. Biotherapeutic approaches to pancreatic cancer. Expert Opin Biol Ther 2003; 3: 319-37 (Retracted in 2012).
PCT International Search Report and the Written Opinion dated Mar. 2, 2012, in International Appl. No. PCT/US2011/001735, filed Oct. 7, 2011. (9 pp.).
Office Action dated Sep. 30, 2014, in U.S. Appl. No. 13/883,061, filed May 2, 2013.
Bold et al. Gemcitabine-Induced Programmed Cell Death (Apoptosis) of Human Pancreatic Carcinoma Is Determined by Bcl-2 Content. Ann Surg Oncol 6:279-285, 1999.
Chai, X. et al. Metformin Increases Sensitivity of Pancreatic Cancer Cells to Gemcitanine by Reducing $CD_{133}$+ Cell Populations and Suppressing ERK/$P_{70}$S6K Signaling. Scientific Reports, 5:14404. www.nature.com/scientificreports. Published Sep. 22, 2015 (11 pages).
Rangarajan, P. et al. Crocetinic acid inhibits hedgehog signaling to inhibit pancreatic cancer stem cells. Oncotarget, vol. 6, No. 29, 27661-27673. Published Aug. 13, 2015.
Tang, F-Y et al. Lycopene inhibits growth of human colon cancer cells via suppression of the Akt signaling pathway, Mol. Nutr. Food Res. 2008, 52, 646-654.
Burris III, H.A. Improvements in Survival and Clinical Benefit With Gemcitabine as First-Line Therapy for Patients With Advanced Pancreas Cancer: A Randomized Trial. Journal of Clinical Oncology, vol. 15, No. 6 (Jun. 1997): pp. 2403-2413.
Grunewald, R. et al. Saturation of 2',2'-diflourodeoxycytidine 5'-triphosphate accumulation by mononuclear cells during a phase I trial of gemcitabine. Cancer Chemotherapy and Pharmacology (1991) 27: 258-262.
Tempero, M.A. et al. Pancreatic Adenocarcinoma, Version 2.2012: Featured Updates to the NCCN Guidelines. J. Natl Compr Canc Netw. Jun. 1, 2012; 10(6): 703-713 (22 pages).
Samulitis et al. Gemcitabine resistant pancreatic cancer cell lines acquire an invasive phenotype with collateral hypersensitivity to histone deacetylase inhibitors. Cancer Biology & Therapy 16:1, 43-51, Jan. 2015.
May, R. et al. Doublecortin and CaM Kinase-like-1 and Leucine-Rich-Repeat-Containing G-Protein-Coupled Receptor Mark Quiescent and Cycling Intestinal Stem Cells, Respectively. *Stem Cells*. 2009; 27(10) 2571-2579.
Office Action (Final Rejection) dated Jun. 2, 2015, in U.S. Appl. No. 13/883,061, filed May 2, 2013.
Office Action dated Mar. 17, 2016, in U.S. Appl. No. 13/883,061, filed May 2, 2013.
Office Action (Final Rejection) dated Nov. 15, 2016, in U.S. Appl. No. 13/883,061, filed May 2, 2013.

* cited by examiner

HPLC purified crocetinic acid

LC/MS of purified crocetinic acid $^1$H NMR of purified crocetinic acid in $d_6$-DMSO

IN VIVO METHOD FOR TREATING, INHIBITING, AND/OR PROPHYLAXIS OF CANCER, SUCH AS PANCREATIC CANCER

CROSS-REFERENCE TO RELATED APPLICATIONS

This is a continuation-in-part (CIP) application of prior U.S. application Ser. No. 13/883,061, filed May 2, 2013, which is a U.S. National Stage application under 35 U.S.C. § 371 of International Application No. PCT/US2011/001735, filed Oct. 7, 2011 (WO 2012/060854 A1, May 10, 2012), which claims priority based on prior U.S. Provisional Application Ser. No. 61/344,879, filed Nov. 2, 2010, all of which are hereby incorporated herein in their entirety by reference.

STATEMENT REGARDING FEDERALLY SPONSORED RESEARCH OR DEVELOPMENT

The work leading to the present invention was supported by the U.S. Government, and specifically the U.S. Department of Veterans Affairs and the National Institute of Health. This work was supported by NIH RO-1 CA 151727, and University of Kansas Cancer Center Pilot Project Award to AD. The U.S. Government, therefore, has certain rights in the invention.

FIELD AND BACKGROUND OF THE INVENTION

The present invention is generally directed to cancer prevention, treatment and therapy, and more particularly to in vivo methods for treating pancreatic cancer using a purified fraction of crude crocetin, including crocetinic acid.

Cancer is a major public health problem in the United States and many other parts of the world. Currently, one in four deaths in the United States is due to cancer. Pancreatic cancer is the fourth leading cause of cancer deaths in developing countries and worldwide and about more than 250,000 cases are diagnosed annually.

There is a significant increase in cancer deaths due to pancreatic cancer (31,000 deaths in 2007 to approximately 37,460 deaths in 2012) in the United States in recent days and there is no significant treatment available at present for pancreatic cancer (Reference 1). There are reports on the use of saffron to treat various diseases, particularly cancer, by the ancient Indian, Egyptian, and Chinese cultures. Saffron is present in the dry stigmas of the plant *Crocus sativus* L., and is used as a spice and a food colorant (References 2-6). Crocetin is a carotenoid extract from the stigma of saffron flower (*Crocus sativus*) and is an amphiphilic terpenoid. By structural analysis, it is a C-18 polyunsaturated carbon chain with COOH group at each end. It is used as anticancer drug in folklore Chinese, Indian, and Egyptian herbal medicine. It is reported to inhibit intracellular nucleic acid and protein synthesis (References 6-7). Experimental study on rat and human colon adenocarcinoma cells, pancreatic and breast cancer cells demonstrated promising effects on cancer (Reference 8). Crocetin inhibits pancreatic cancer cell proliferation and tumor progression in a xenograft mouse model. Comprehensive chemical analysis of saffron extract has demonstrated that major constituents include carotenoids, and in particular, crocetin (References 7-8).

It has been demonstrated that commercial or crude crocetin inhibited in vitro pancreatic cancer cell proliferation and tumor progression in a xenograft mouse model (References 7-8). It was reported first in 1990s and confirmed in recent years that saffron extract inhibited growth of malignant cells in vitro and also in vivo (References 9-11). Inhibition of DNA, RNA and protein synthesis was demonstrated in three human malignant cells exposed to crocetin (Reference 12) and the mechanism of action was reported through suppression of the activity of DNA-dependent RNA polymerase II (References 13-14).

Another study also demonstrated that crocetin reduces in vitro histone H1-DNA interaction and interfered with transcription (Reference 15). Crocetin and carotenoids in general, showed cytotoxic effects on a range of tumors and malignant cells (Reference 8).

During the last decade, a number of studies in animal model systems have demonstrated an antitumor effect of saffron (Reference 8). One in vivo study reported that crocetin has antitumor activity in a lung cancer animal model by scavenging free radicals and drug metabolizing enzymes (Reference 16). In a recent in vitro study, crocetin demonstrated significant reduction of cell proliferation in both MCF-7 and MDA-MD-231 breast cancer cells (Reference 17).

Collectively, these studies provide strong evidence of the antitumor activity of crocetin. Given the potential importance of crocetin, this series of experiments was designed to examine the effect of crocetin on pancreatic adenocarcinoma cells and also to evaluate whether it has an antitumorigenic effect on pancreatic cancer in an athymic (nude) mice model.

ASPECTS OF THE INVENTION

The present disclosure is directed to various aspects of the present invention.

One aspect of the present invention includes purifying or fractionating crude crocetin to obtain a more potent agent than crude crocetin.

Another aspect of the present invention includes a novel crocetin compound.

Another aspect of the present invention includes a novel crocetin compound that is 50-times more potent than the crude crocetin.

Another aspect of the present invention includes a novel crocetin compound that has a low toxicity.

Another aspect of the present invention includes crocetinic acid.

Another aspect of the present invention includes the use of crocetinic acid as an anti-cancer agent.

Another aspect of the present invention includes the use of crocetinic acid in inhibiting proliferation of cancer cells.

Another aspect of the present invention includes the use of crocetinic acid in inhibiting proliferation of pancreatic cancer cells.

Another aspect of the present invention includes the use of crocetinic acid in stimulating apoptsis in cancer cells.

Another aspect of the present invention includes the use of crocetinic acid in stimulating apoptsis in pancreatic cancer cells.

Another aspect of the present invention includes the use of crocetinic acid in therapy, treatment, and/or prevention of cancer.

Another aspect of the present invention includes the use of crocetinic acid in therapy, treatment, and/or prevention of pancreatic cancer.

Another aspect of the present invention includes the use of crocetinic acid in therapy, treatment, and/or prevention of pancreatic cancer, in combination with other anticancer agent(s).

Another aspect of the present invention includes a composition including crocetinic acid.

Another aspect of the present invention includes a pharmaceutical formulation including crocetinic acid.

Another aspect of the present invention includes a diagnostic tool, marker, probe, assay, composition, and/or formulation including crocetinic acid.

Another aspect of the present invention includes an in vivo method of inhibiting tumor growth, which includes providing a subject with a tumor, and administering an effective amount of a compound, composition, and/or a pharmaceutical formulation including crocetinic acid to the subject.

Another aspect of the present invention includes an in vivo method of inhibiting proliferation of tumor cells, which includes providing a subject with a tumor including cells, and administering an effective amount of a compound, composition, and/or a pharmaceutical formulation including crocetinic acid to the subject.

Another aspect of the present invention includes an in vivo method of stimulating apoptosis in tumor cells, which includes providing a subject with a tumor including cells, and administering an effective amount of a compound, composition, and/or a pharmaceutical formulation including crocetinic acid to the subject.

Another aspect of the present invention includes a method of impairing or preventing self-renewal of cancer stem cells, which includes providing a predetermined amount of cancer stem cells, and subjecting the cancer stem cells to an effective amount of a compound, composition, and/or a formulation including crocetinic acid.

In summary, pancreatic cancer is the fourth leading cause of cancer deaths in the United States and no significant treatment is presently available. Previously, we demonstrated that commercial crocetin treatment has potent antimitotic effects on both in vitro and in vivo pancreatic cancer xenograft models. We have recently purified novel crocetin compound from commercial or crude crocetin compound using HPLC (high performance liquid chromatography) and LC/MS (liquid chromatography/mass spectrometry). One of the fractions showed more potency than commercial or crude crocetin in vitro inhibiting proliferation and stimulating apoptosis. Our studies demonstrate that the compound had significant cytotoxicity against pancreatic cancer cells in both a dose- and time-dependent manner. Treatment with purified crocetinic acid decreased the number and size of the primary and secondary pancospheres in a dose dependent manner, suggesting that crocetinic acid targets CSCs (cancer stem cells). To understand the mechanism of inhibition of pancospheres, the signaling pathways affected by crocetinic acid were dissected. Sonic hedgehog (Shh) upon binding to its cognate receptor patched, allows smoothened to accumulate and activate Gli transcription factor. Treatment with crocetinic acid inhibited the expression of both Shh and smoothened in the pancreatic CSCs with concomitant reduction of the expression of a novel pancreatic CSC marker, DCLK-1 (Doublecortin Calcium/Calmodulin-Dependent Kinase-1). Furthermore, it inhibited the expression of patched-1 and Gli-1, downstream targets of the hedgehog signaling pathway. Crocetinic acid also inhibited tumor formation in pancreatic cancer in vivo xenograft models.

Taken together, our data suggest that crocetinic acid effectively inhibits pancreatic CSCs by down-regulating the sonic hedgehog pathway, thereby inhibiting tumorigenesis.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

One of the above and other aspects, novel features and advantages of the present invention will become apparent from the following detailed description of the non-limiting preferred embodiment(s) of invention, illustrated in the accompanying drawings, wherein:

FIG. 7A illustrates western blots of onic Hedgehog signaling pathways proteins (sonic hedgehog, Gli-1, SUFU, Smoothened with beta-actin) expressions in treated lanes of I (CC), 2 (PC #5), 3 (PC #3) and 4 (PC #1).

FIG. 7B illustrates sonic hedgehog target genes: Patched, p21, cyclin D1 with actin treated by CC (Lane 1) and PC #5 (Lane 2), PC #3 (Lane 3) and PC #1 (Lane 4).

FIG. 7C illustrates spheroid formation assay. Stemness pancreatic cancer cells ware determined using spheroid assay in PC versus CC in different concentrations (0, 1, 5, 10, 20 µM); and FIG. 7D illustrates DCLK1 expression. Western blot analysis of DCLK1 after treatment of Mia-PaCa2 cells treated with 10 mM of CC and PC of #5, #3 and #1 HPLC fractions.

DETAILED DESCRIPTION OF THE PREFERRED EMBODIMENT(S) OF THE INVENTION

Figure 1A:
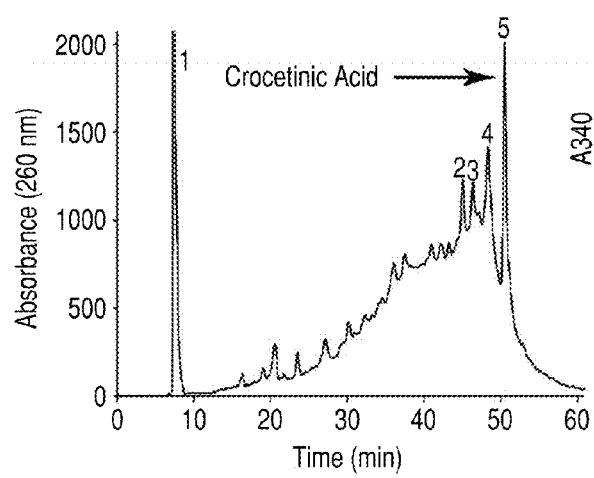
FIG. 1A illustrates HPLC purification of commercial crocetin. Crocetin was purified by preparative HPLC on Agilent 1050 series HPLC equipped with diode array detector and fractions were collected in Gilson fraction collector.

Commercial or crude crocetin is a combination of multiple components present as assessed by HPLC (high performance liquid chromatography) and LC/MS (liquid chromatography/mass spectrometry). These compounds differ from crocetin in the number of sugars and methyl groups. Therefore, our approach here is to characterize subcomponents present in crude preparations of crocetin and to identify stable crocetin using preparative HPLC and LC/MS. All the fractions are tested for proliferation and apoptosis as markers of anti-tumorigenic effect.

Recent evidence suggests the existence of a small population of tumorigenic stem cells responsible for tumor initiation, metastasis and resistance to chemotherapy and radiation. Identification of the regulatory mechanisms and signaling pathways involved in cancer stem cells (CSCs) will help in designing novel agents to target this refractory cell population in pancreatic cancers.

We are currently investigating the mechanisms by which purified crocetinic acid, a carotenoid molecule isolated from saffron, inhibits growth of pancreatic cancer in vitro and in vivo models. Our studies demonstrate that the compound had significant cytotoxicity against pancreatic cancer cells in both a dose- and time-dependent manner. Pancreatic CSCs can be allowed to divide and grow in ultra-low binding tissue culture dishes to form multicellular spheroids called pancospheres (Reference 18).

Treatment with purified crocetinic acid decreased the number and size of the primary and secondary pancospheres in a dose dependent manner, suggesting that crocetinic acid targets CSC. To understand the mechanism of inhibition of pancospheres, the signaling pathways affected by crocetinic acid were dissected. Aberrant activation of Sonic Hedgehog signaling pathway has been associated with renewal of cancer stem cells, and in the development of several solid cancers. Sonic hedgehog (Shh) upon binding to its cognate receptor patched, allows smoothened to accumulate and activate Gli transcription factor (Reference 18). Treatment with crocetinic acid inhibited the expression of both Shh and smoothened in the pancreatic CSCs with concomitant reduction of the expression of a novel pancreatic CSC marker, DCLK-1 (Doublecortin Calcium/Calmodulin-Dependent Kinase-1). Furthermore, it inhibited the expression of patched-1 and Gli-1, downstream targets of the hedgehog signaling pathway (Reference 18). Crocetinic acid also inhibited tumor formation in pancreatic cancer in vivo xenograft models. Taken together, these data suggest that crocetinic acid effectively inhibits pancreatic CSCs by downregulating the sonic hedgehog pathway, thereby inhibiting tumorigenesis.

Materials and Methods

Reagents

Anti-PCNA (proliferating cell nuclear antigen) and monoclonal antibodies of phospho-EGFR from Cell Signaling (Danvers, Mass.), EGFR from BD Biosciences (San Jose, Calif.), Bcl-2 from Calbiochem (San Diego, Calif.), Bax polyclonal antibodies from Santa Cruz Biotechnology (Santa Cruz, Calif.), and β-actin monoclonal from Sigma Chemical Co. were obtained (St. Louis, Mo.) respectively. The FITC (fluorescein isothiocyanate) Annexin V/Dead Cell Apoptosis assay kit was purchased from Invitrogen (Life Technologies, Green Island, N.Y.). Click-it EdU micopalte proliferation assay kit was purchased from Invitrogen (Life Technologies, Green Island, N.Y.). Peptamen was purchased from Nestle (Los Angeles, Calif.).

Cell Lines, Culture Conditions and Treatment

The human pancreatic adenocarcinoma cell lines MIA-PaCa-2, BxPC3, Capan-1 and ASPC-1 were obtained from the American Type Culture Collection (ATCC, Manassas, Va., USA) and grown in Dulbecco's modified Eagles medium (DMEM, Sigma Chemical Co, St Louis, Mo.) supplemented with 1 mM sodium pyruvate (Fisher Chemical Company), 100 U/ml of penicillin and 100 U/ml of streptomycin (Sigma Chemical Co, St Louis, Mo.) and 10% FBS (Hyclone, Road Logan, Utah) at 37° C. in a humidified tissue culture incubator containing 5% CO2 and 95% air. ~70% confluent cells were treated with different concentrations (1-50 µM) of purified crocetinic acid and commercial crocetin for 72 h.

Purification of Crude Crocetin by HPLC and Characterization by LC/MS

Crocetin was purified by preparative HPLC on Agilent 1050 series HPLC equipped with diode array detector and Gilson fraction collector. Chromatographic elution was performed on Alltech Econosphere C18 column (250×10 mm, 10 µm particles) at a flow rate of 2 mL/min for the initial 4 minutes and then 3 mL/min, with a gradient of 100% solvent A (0.1% Formic acid in water) for 4 min, then 0% to 100% of solvent B (methanol) in next 60 min, then a linear gradient of 100% solvent B for the next 10 min, then 0% to 100% of solvent A in next 1 min, and then a linear gradient of 100% solvent A for the next 15 min. The fractions are collected using automated Gilson fraction collector.

Click-It EDU Micro-Plate Proliferation Assay

Pancreatic cancer cells were plated at desired density onto 96-well corning tissue culture plates. After 24 hours, cells were treated for 72 hours with different concentrations (1-50 µM) of purified crocetin and crude/commercial crocetin. Cells were labelled with Click-it EdU and were fixed. Then fixed cells were incubated with anti-Oregon Green antibody conjugated to horseradish peroxidase and measured flurescent product (excitation/emission~568/585).

Preparative HPLC

Figure 3A:
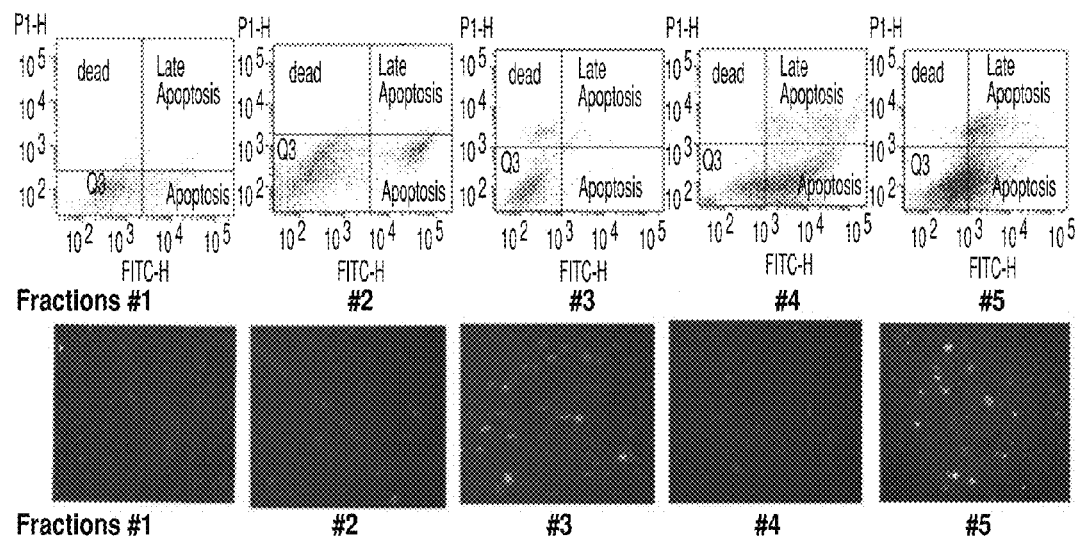
FIG. 3A illustrates apoptosis using different purified fractions. Apoptosis assay using apoptosis kit using different concentrations (Only 10 µM of 5 fractions was used for apoptosis also using flow cytometry and fluorescence microscopy)

Commercial crocetin was fractionated by preparative HPLC on an Agilent 1050 series. Commercial crocetin contains at least 5 major components and several minor components (FIG. 3A). One of last fractions was crocetinic acid (FIG. 3A) which was collected and analyzed by LC/MS. Each compound was purified and characterized using LC/MS for biological activity, described below, because these crocetin esters could be developed as pro-drugs.

LC/MS

Figure 3B:
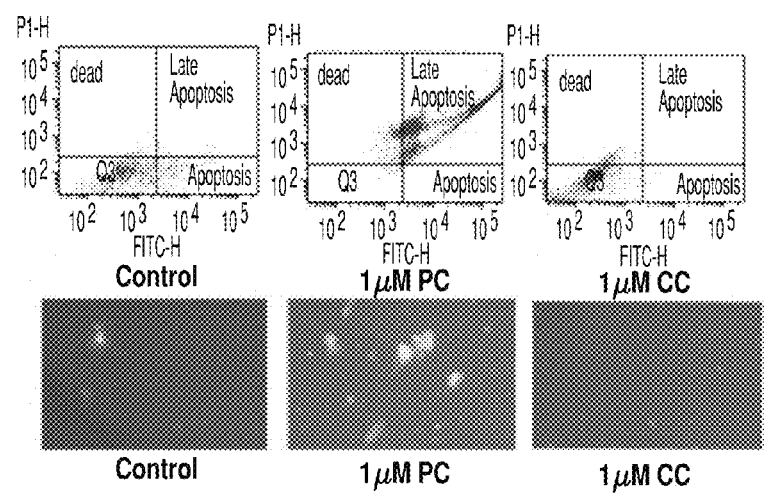
FIG. 3B illustrates comparison of inhibition of apoptosis in Panc-1 cells. Panc-1 cells were incubated with PC and CC. Only 1 and 10 µM of PC and CC were presented for apoptosis using flow cytometry. Similarly, only 1 µM was presented using fluorescence microscopy for apoptosis.

LC/MS analysis was carried out on the HPLC collected fraction of crocetin (FIG. 3A), using ABI 2000 QTrap. The crocetin fraction of HPLC demonstrated a single peak in LC/MS (FIG. 3B) with the correct mass for crocetin dicarboxylic acid. (Crocetin purification was done in collaboration with William Gutheil, Associate Professor of Pharmaceutical Sciences, UMKC.)

Flow Cytometric Analysis

After treatment with crocetin (50, 100 and 200 µM) for 72 hours, MIA-PaCa-2 cells were collected by trypsinization, fixed in 70% ethanol, washed in phosphate-buffered saline (PBS) and the cells were counted. After centrifugation, the cells were resuspended in PBS containing RNase (100 µg/ml) 37° C. for 30 min. After digestion of cellular RNA, cells were pelleted and resuspended in fresh PBS containing propidium iodide (0.5 mg/ml). Data were acquired on a FACS (flow cytometry) Scan flow cytometer (Becton Dickinson) and analyzed by using the Cellquest software.

NMR

Agilant NMR (nuclear magnetic resonance) system was used for purified #5 fractions separated from commercial crocetin.

Animals

Six-eight weeks old athymic female outbreed nude mice (nu/nu) were obtained from Charles River Laboratories, (Wilmington, Mass.) and were used for tumor development. All animals were maintained in a sterile environment and daily 12-hr light/12-hr dark cycle. All the mice were maintained according to standard guidelines of American Association for the Accreditation of Laboratory Animal Care with the approval of the Institutional Animal Care and Use Committee of the Kansas City VA Medical Center.

Tumor Production in Athymic Female Nude Mice

MIA-PaCa-2 cells ($2.5 \times 10^6$) were injected into the right hind leg of each mouse for the development of tumor. The mice were divided into two groups (6 mice per group) with a control group and crocetin treatment group. After development of palpable tumor, the tumor size was measured twice in a week. When tumors are well established (approximately 0.34 cm$^3$); treatment was started. The treatment group received crocetin at 0.5 mg/kg/day orally dissolved in 15 ml of peptamen for 12 hours during dark for 30 days and the dose is in agreement with other investigators (References 14, 17, 20 and 27). Tumor size was monitored twice weekly, and its volume calculated as V=(a×b)$^2$/2, where a=length and b=width. Control group received only peptamen. The mice were given solid food during light time following liquid peptamen diet at dark. All mice were sacrificed after 30 days following treatment and tumors were taken out and stored at −80° C.

Western Blot Analysis

The immuno-Western blot analyses were the same as described earlier by Banerjee et al. (Reference 26). Briefly, MIA-PaCa-2 and BxPC-3 cells following treatment with or without crocetin and tumor samples were homogenized. Then, both cell and tumor lysates were spun at 18000 g for 1 hr at 4° C., and the supernatants were collected for immunodetection. Protein concentration was measured by using the Comassie blue reagent assay (Pierce, Rockford, Ill.). Equal amount of protein were resolved in 10% SDS-PAGE, transferred onto nitrocellulose membranes. Membranes were blocked with super block (Pierce, Rockford, Ill.) followed by incubation with appropriate primary antibodies at 4° C., overnight. The antigen-antibody reactions were detected with HRP-conjugated anti-rabbit or anti-mouse IgG for one hour in room temperature. Immunoreactions were visualized by the ECL (electrochemiluminescence) chemiluminescence reagent kit (Pierce, Rockford, Ill.) and relative expression of proteins were calculated by densitometric analyses using ID image Analysis Software version 3.6 (Eastman Kodak Company, Rochester, N.Y.).

Immunohistochemistry

Immunohistochemical analysis was performed according to our previous described method (27) using Zymed broad range immunohistochemical kits (Zymed Laboratories, CA). Tumor tissue samples were fixed in 4% buffered formalin and embedded in paraffin. The serial sections of 5 µm were cut. The tissue sections were deparaffinized and were hydrated in different concentrations of ethanol (i.e. 100%, 90%, 70%, and 50%). Endogenous peroxidase activity was blocked at room temperature by incubating in hydrogen peroxide in methanol (1:9). Slides were washed with PBS (phosphate buffered saline) and nonspecific binding was blocked by blocking solution for 10 min. The sections were incubated with respective primary antibody in a humidified chamber at 4° C. overnight. The tissues were incubated with biotynylated secondary antibody (Zymed kit). The slides were then incubated with HRP (horseradish peroxidase) linked enzyme conjugate for 10 min. Positive reactions were visualized by incubating slides with stable 3,3'-diaminobenzidine (DAB) solution (Zymed kit) and counterstained with haematoxylin. The slides were dehydrated and mounted in permount for microscopic examination.

FITC Annexin V/Dead Cell Apoptosis Kit

FITC Annexin V and PI for flow cytometry provide a rapid and convenient assay for apoptosis. Treated and control cells were incubated with annexin V conjugate and propidium iodide (PI). Then cells were deposited onto slides for fluorescence microscopy. Cells were also used for flow cytometry analysis for live, apoptotic and dead cells using annexin V conjugated to green-fluorescent FITC dye and propidium iodide (PI). Propidium iodide stains necrotic cells with red fluorescence whereas green FITC dye stains apoptotic cells.

Pancospheriod Formation Assay

Spheroids were prepared as previously described (Reference 17). Briefly, 1000 cells/well in DMEM/F12 (Invitrogen, France) supplemented with EGF (20 ng/ml, Invitrogen) and B27 (1×, Invitrogen) were distributed in in ultra-low attachment plates 6 well plates. Plates were placed in a humidified atmosphere of 5% CO2 at 37° C. Numbers of pancosphers formation, after 6-8 days culture, were counted under a light microscopy and quantified by Celigo software.

Statistical Analysis

All experiments were performed in triplicate for each of the observations. Each data represents the mean±standard deviation from three separate experiments. Statistical analysis was performed between the groups of data by paired Student's t-test. P-value less than 0.05 were considered as statistically significant.

Results

Purification of Crude Crocetin by HPLC and Characterization by LC/MS

For the commercial preparations of crocetin used in our studies, we used preparative HPLC to fractionate crude crocetin and LC/MS to characterize the fractions.

Preparative HPLC

Commercial crocetin was fractionated by preparative HPLC on an Agilent 1050 series. Commercial crocetin contains at least five (5) major components and several minor components (FIG. 3A). One of the last fractions was crocetinic acid (FIG. 1A) which was collected and analyzed by LC/MS. Each compound was purified and characterized using LC/MS for biological activity described below because these crocetin esters could be developed as pro-drugs.

LC/MS

LC/MS analysis was carried out on the HPLC collected fraction of crocetin (FIG. 1A), using ABI 2000 QTrap. The crocetin fraction of HPLC demonstrated a single peak in LC/MS (FIG. 1B) with the correct mass for crocetin dicarboxylic acid.

Figure 1B:
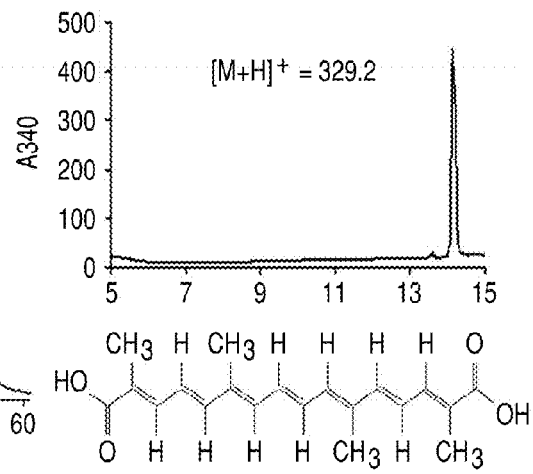
FIG. 1B illustrates LC/MS purified crocetin fraction eluted from HPLC. LC/MS analysis was carried out on the fractions collected, using ABI 2000 QTrap with an electron spray ionization (ESI) source, interfaced to an Agilent 1100 series HPLC system equipped with diode array detector.
Figure 1C:
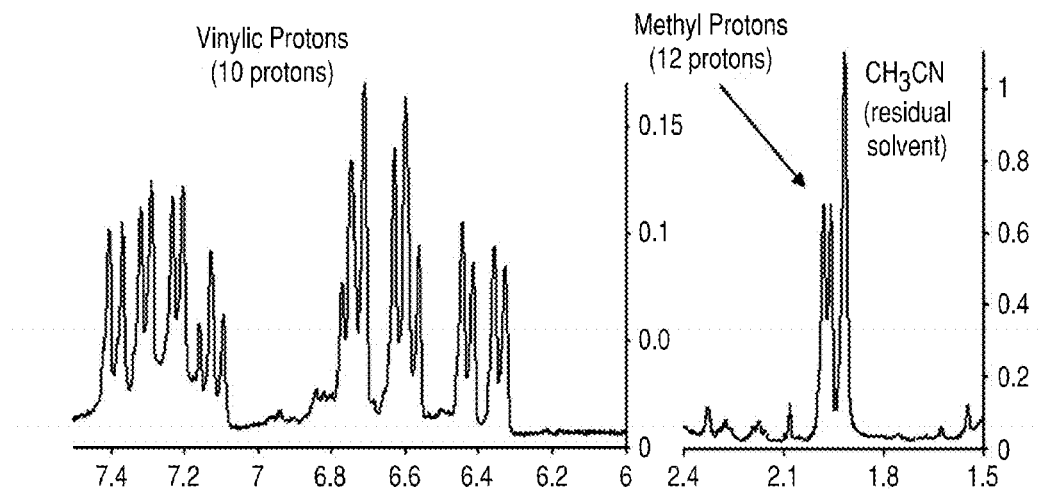
FIG. 1C illustrates NMR Spectroscopy. $H^3$ NMR spectroscopy analysis was carried through vinyl and methyl protons of HPLC purified #5 fraction.

NMR $H^3$ NMR spectroscopy by both venyl and methyl protein analysis suggested that the #5 fractions of HPLC is crocetinic acid (FIG. 1C).

Figure 2A:
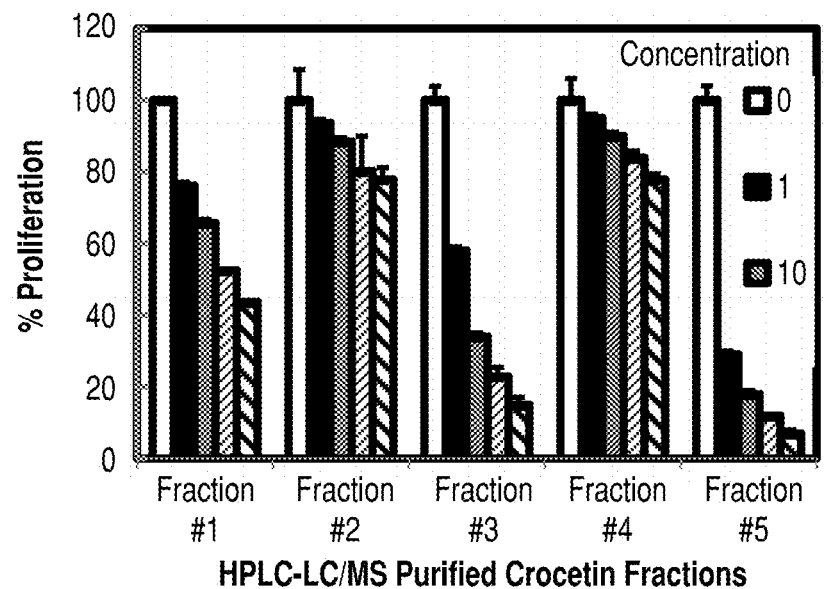
FIG. 2A illustrates different purified HPLC fractions for click-it-edu proliferation assays using Panc-1 cell lines.
Figure 2B:
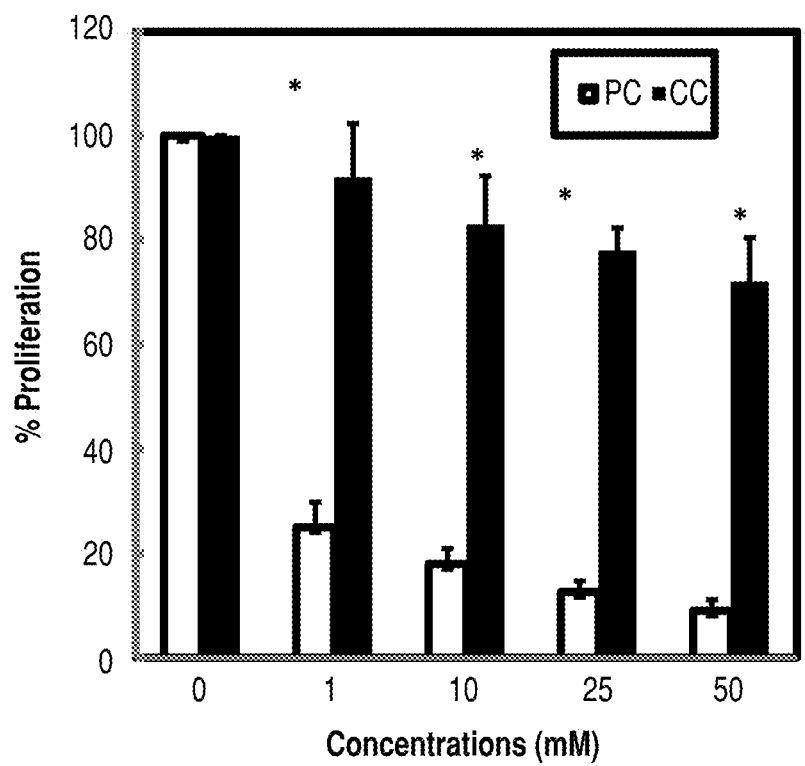
FIG. 2B illustrates comparisons of proliferation purified #5 fraction as crocetinic acid (PC) and commercial crocetin (CC)
Figure 2C:
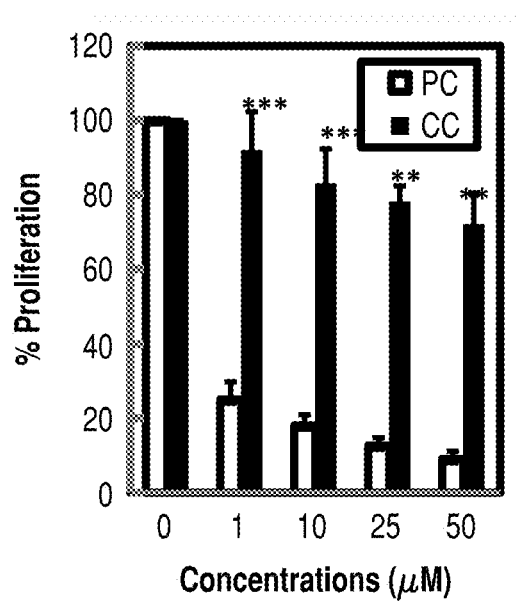
FIG. 2C illustrates apoptosis assay using TUNEL (Terminal Deoxynucleotidyl Transferase dUTP Nick Labeling) assay kit of different HPLC purified fractions.
Figure 2D:
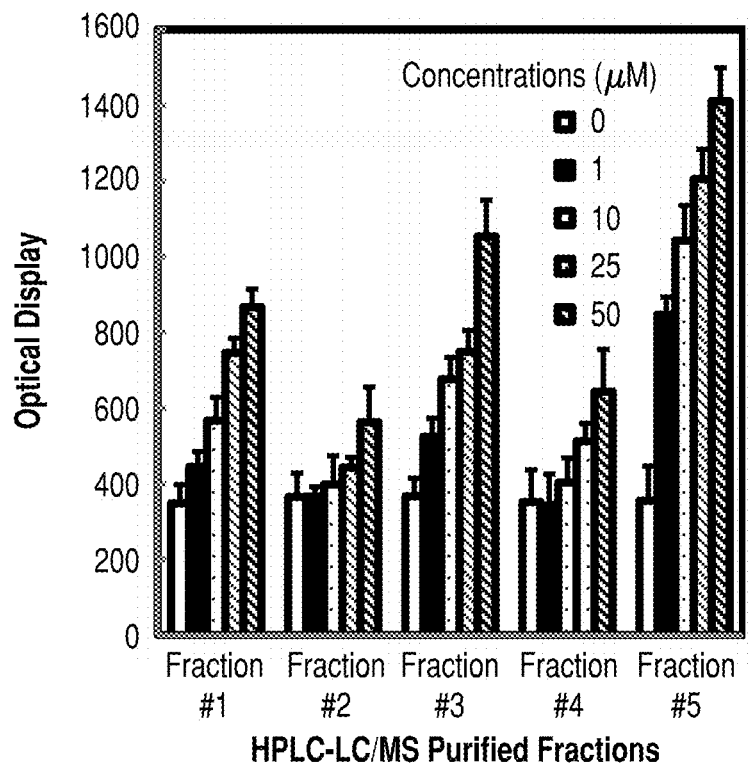
FIG. 2D illustrates comparison of apoptosis using TUNEL apoptosis assay kit of PC and CC.

Proliferation and Apoptosis Assay with Crude Crocetin and with Newly Purified Crocetin in Panc-1 and BxPC3 Pancreatic Cancer Cells Our data demonstrates that purified crocetin obtained in good yield from crude crocetin by 0.01 mM sodium hydroxide treatment following HPLC and LC/MS and demonstrated about 50-times more potent in proliferation and apoptosis assays (FIGS. 2A and 2B). We treated Panc-1 pancreatic cancer cells with either purified crocetin or PC (fraction 5 of FIG. 2A) derived from alkaline treatment or crude commercial crocetin or CC (1 and 10 µM concentrations) for 48-72 hours. We have also used higher doses (25, 50 and 100 µM) in this experiment and it needs about 50-100 concentration of CC for inhibition of proliferation and increase of apoptosis at the level of 1 and 10 µm of PC. Treated cells were then labeled with Brdu and cells were assayed by Invitrogen Click-it Edu fluorimetric microplate proliferation kit and apoptosis assay kit. Alkaline treatment of crude crocetin following HPLC showed more potency than crude crocetin in both apoptosis assay by Annexin5-FITC Flow Cytometry and Fluorescence microscopy (FIG. 2C).

Figure 4A:
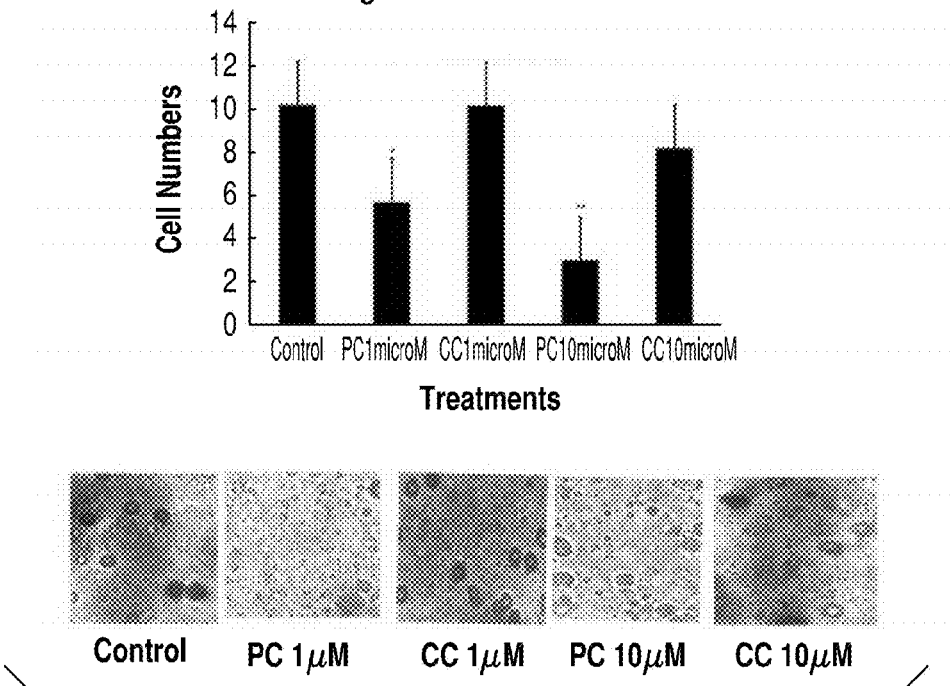
FIG. 4A illustrates effect of purified crocetin (PC) and crude crocetin (CC) on migration of Panc-1 cells. Panc-1 cells were incubated with PC and CC at concentrations of 1 and 10 µM in Bowden chamber for 24 hours and migration was studied. PC at 1 and 10 µM significantly inhibited migration than CC.
Figure 4B:
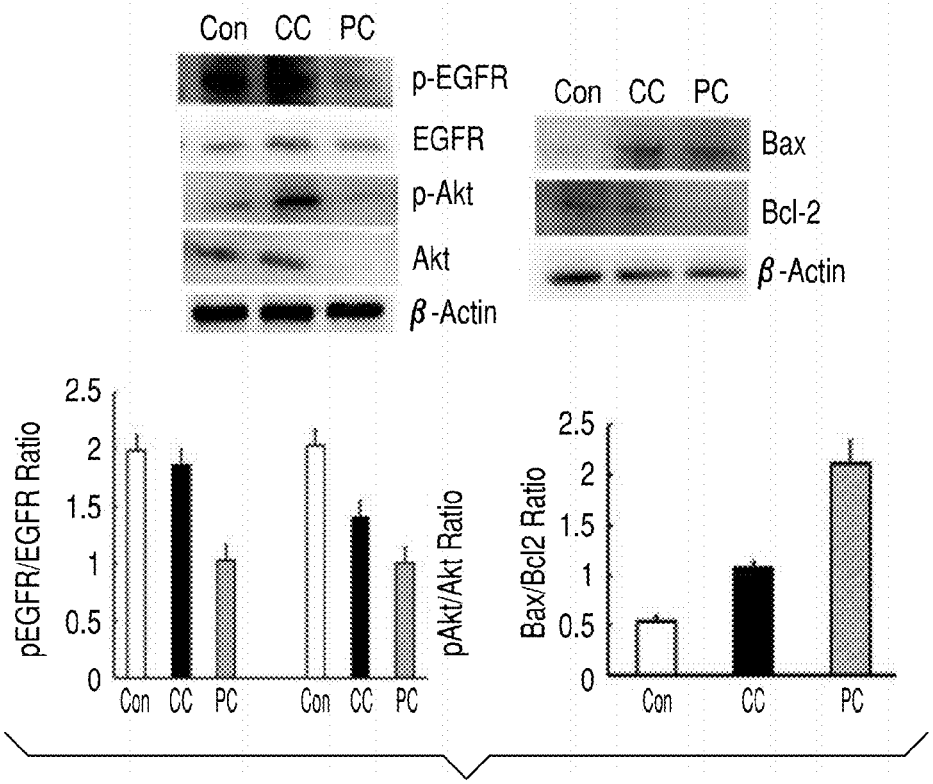
FIG. 4B illustrates effect of purified crocetin (PC) and crude crocetin (CC) on EGFR (epidermal growth factor receptor), Akt signaling and Bax/Bcl-2 on Panc-1 cells. Left panel shows the showed EGFR activity both phosphorylated and total EGFR and also Akt phosphorylation that are significantly inhibited by 10 mM PC; Right panel shows decrease of Bcl-2 and increase of Bax/Bcl-2 ratio that confirms apoptosis.

Proliferation and Apoptosis Assay with all Five (5) Purified Crocetin in Panc-1 Pancreatic Cancer Cells We have generated new preliminary data using five fractions separated from crude crocetin (FIG. 1A). We treated Panc-1 cells with all 5 fractions and peaks #1, #3 and #5 (crocetinic acid) show promising effect on inhibiting proliferation and stimulating apoptosis (FIG. 4A). Peak #5 (crocetinic acid) showed most potent effect and the effect is 50-times greater than crude crocetin (FIG. 4). The remaining two peaks showed little inhibition of proliferation using in vitro models. This observation needs to be confirmed with other batches of separation of crude crocetin.

Status of Proliferation and Apoptotic Signature Proteins

Figure 5:
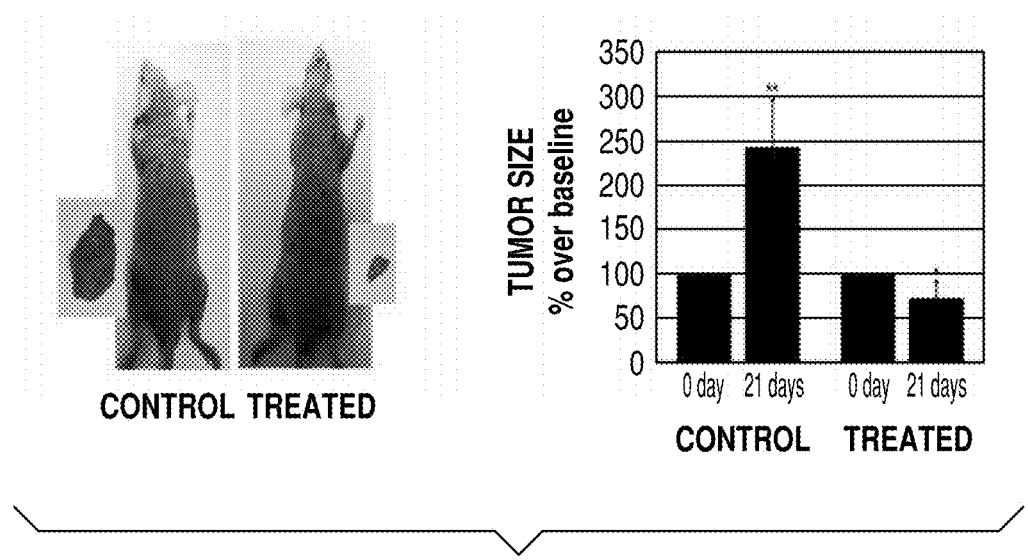
FIG. 5 illustrates pancreatic cancer xenograft tumor growth in athymic (nude) mice. Tumor growth is significantly inhibited after crocetinic acid (0.5 mg/kg) treatment in comparison to control, as shown in the insets of the xenograft tumors removed from the respective mice (left). The tumor size was measured (right) from the start date of crocetin treatment (0 day) to end date of crocetin treatment (21 days) in comparison to control (no treatment). Number of animals is 5 in the control and treated group.
Figure 6A:
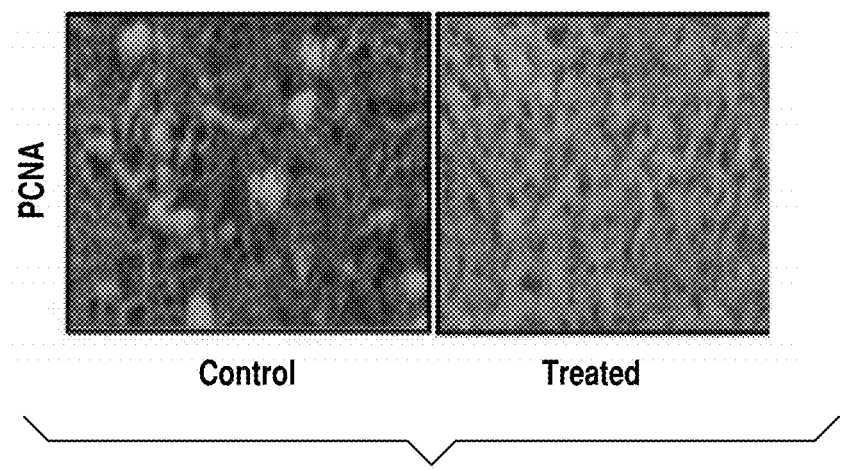
FIG. 6A illustrates expression of PCNA (proliferating cell nuclear antigen). Cell proliferation in tumor tissues, obtained from athymic mice as depicted in FIG. 5, was evaluated by staining for PCNA using histochemical analysis. PCNA expression, as indicated by the dense red collections of stain in untreated, was significantly decreased in crocetin-treated tumors, indicating decreased proliferation associated with crocetinic acid treatment.
Figure 6B:
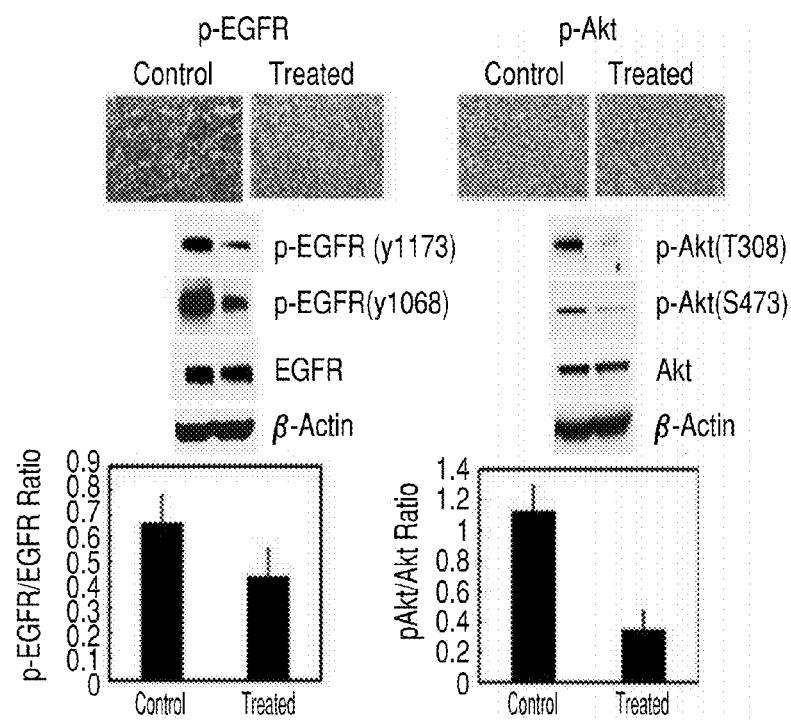
FIG. 6B illustrates expression of EGFR and Akt. Tissue sections were obtained from human pancreatic cancer tumors growing in nude mice as described in FIG. 5, and stained for pEGFR and pAkt as described in Materials and Methods section (below). Middle, EGFR and Akt expression of pancreatic tumors from same crocetinic acid-treated and untreated control animals using Western Blot as described in FIG. 4B, was determined. Phophorylated (p-EGFR) and total protein of EGFR and phophorylated Akt and total Akt expressed as ratio between them normalized with b-actin was shown (bottom)

Inhibition of proliferation using click-it microplate assay and stimulation of apoptosis microplate assay suggested 50 times more potent alkali treated purified PC than CC (FIG. 5). Even 1 mM PC showed highly potent inhibition in proliferation and increase in apoptosis than CC (FIG. 5). Apoptosis also showed significant increase in lower doses of PC using flow cytometry and fluorescence microscopy. EGFR phosphorylation is significantly inhibited by 10 mM PC than CC and both Akt expression and phosphoryalation also inhibited by PC (FIG. 6B). This indicates that purified crocetin at lower doses significantly inhibited EGFR signaling pathways which, in turn, affect proliferation.

Effect of Crocetinic Acid on Pancosphere Formation and Sonic Hedgehog Pathway

Recent evidence suggests the existence of a small population of tumorigenic stem cells responsible for tumor initiation, metastasis and resistance to chemotherapy and radiation. Identification of the regulatory mechanisms and signaling pathways involved in cancer stem cells (CSCs) will help in designing novel agents to target this refractory cell population in pancreatic cancers.

We are currently investigating the mechanisms by which purified crocetinic acid, a carotenoid molecule isolated from saffron, inhibits growth of pancreatic cancer in vitro and in vivo models. Our studies demonstrate that the compound had significant cytotoxicity against pancreatic cancer cells in both a dose- and time-dependent manner. Pancreatic CSCs can be allowed to divide and grow in ultra-low binding tissue culture dishes to form multicellular spheroids called pancospheres. Treatment with purified crocetinic acid decreased the number and size of the primary and secondary pancospheres in a dose dependent manner, suggesting that crocetinic acid targets CSCs. To understand the mechanism of inhibition of pancospheres, the signaling pathways affected by crocetinic acid were dissected. Treatment with different fractions particularly HPLC purified fractions 5, 3 and 1 in comparison to commercial crocetin sonic hedgehog is significantly inhibited in all the fractions and rightfully, pathched was increased in comparison to commercial crocetin. Treatment with those fractions also inhibited smoothened, SUFU, and Gli1 including target protein cylinD1. All those fractions inhibited the expression of both Shh and smoothened in the pancreatic CSCs with concomitant reduction of the expression of a novel pancreatic CSC marker, DCLK-1 (Doublecortin Calcium/Calmodulin-Dependent Kinase-1).

Effect of Crocetin on Tumor Regression in Athymic (Nude) Mice

Next, pancreatic cancer cells particularly MIA-PaCa-2 were used for in vivo studies because MIA-PaCa-2 cells are characteristically more aggressive than other pancreatic cancer cells (BxPC-3, Capan-1 and ASPC-1) and have the ability to develop tumors within several weeks of inoculation (Reference 27). MIA-PaCa-2 cells were introduced in the athymic nude-mice for 3-4 weeks until palpable tumor was formed. Then, the mice (six) in each group were treated with or without crocetin (4 mg/kg/day) for 30 days and the tumors were measured twice per week until the mice were sacrificed. The tumor incidence was 100% in all the animals.

Effect of Crocetin In Vivo on PCNA, EGFR Expression and Apoptosis

Figure 6C:
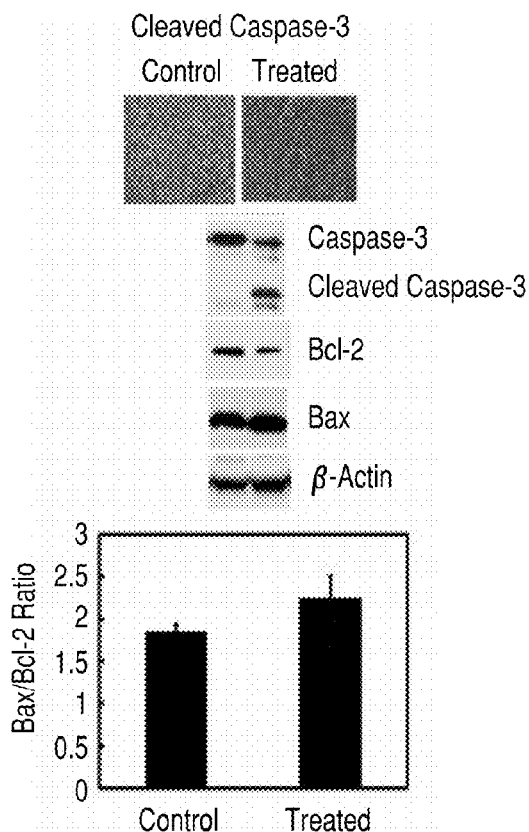
FIG. 6C illustrates apoptosis. Top, tumor tissues were processed for Cleaved Caspase 3 immunohistochemistry. Increased apoptosis in pancreatic cancer xenografts tumors from animals receiving daily crocetinic acid compared with pancreatic cancer xenografts receiving vehicle as control. Caspase 3, Bax and Bcl-2 (middle) expressions of pancreatic tumors from same crocetinic acid-treated and control animals using Western Blot were carried out and Bax/Bcl-2 ratio was also determined (bottom). Columns, mean from six different animals; bars, SD (B and C). *, P<0.05; **, P<0.001 versus untreated control (Student's t test)
Figure 7A:
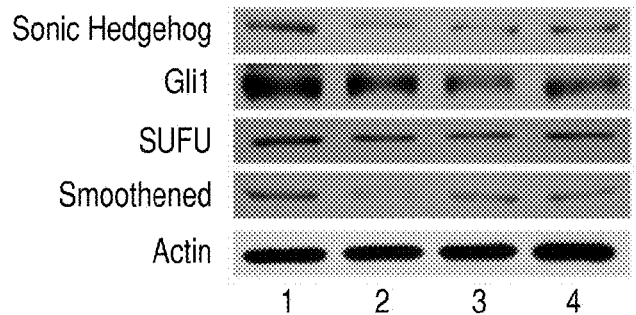
FIGS. 7A-D illustrate analyses of CSC following purified crocetinic acid (PC) treatment.
Figure 7B:
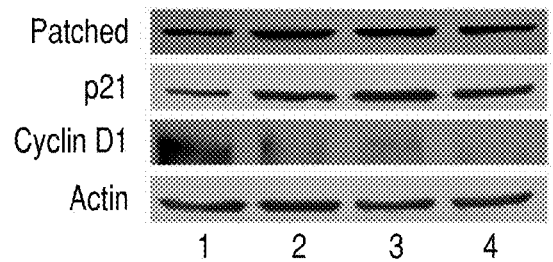
Figure 7C:
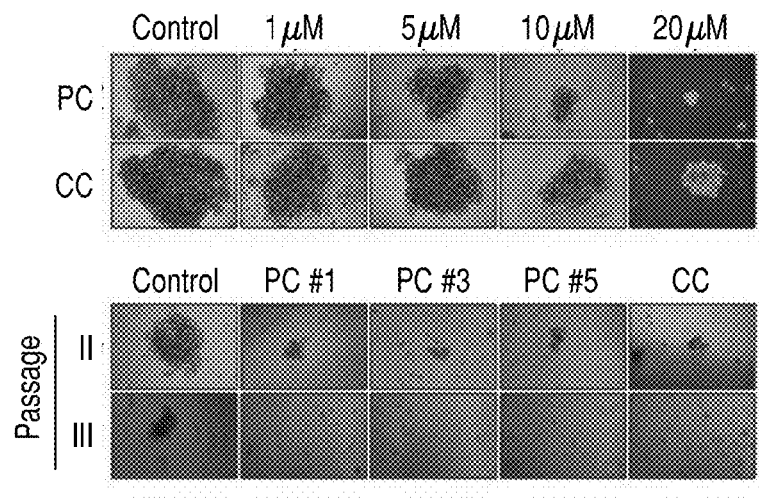
Figure 7D:
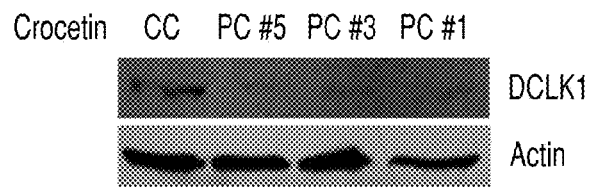

To explore whether the regression of tumor growth by crocetin is due to inhibition of proliferation, apoptotic cell death or both, we first evaluated PCNA (proliferating cell nuclear antigen) expression and then EGFR expression in tumors using histochemical analysis. As shown in FIG. 6A, PCNA positive cells were elevated significantly in untreated samples in comparison to crocetin treated samples. EGFR expression and phosphorylation was significantly reduced in crocetin-treated animals when compared to the untreated samples. Additionally, EGFR activity as determined by the ratio of EGFR phosphorylated form and unphosphorylated form was significantly impaired in the tumors due to crocetin treatment (FIG. 6B). Next, apoptosis by TUNEL assay was investigated in the tumors of mice treated with or without crocetin. TUNEL assay positive cells were elevated markedly in crocetin treated samples as compared to untreated samples (FIG. 6C).

Collectively our experiments indicate that inhibition of tumor growth is due to the induction of apoptosis, as well as inhibition of proliferation. To further confirm the apoptotic effect, the Bax/Bcl-2 ratio was evaluated. As shown in FIG. 6C, expression of Bax protein was increased with a concomitant decrease of Bcl-2 protein.

Discussion

Pancreatic cancer is the fifth leading cause of cancer death in the Western world (References 1 and 19). Pancreatic tumors are highly resistant to current available therapies and the 5-year survival is dismal with a median expected post-diagnosis survival time of five months (References 1, 19 and 20). Owing to poor prognosis, alternative therapies are being investigated. Crocetin, a carotenoid compound derived from saffron, has demonstrated a significant inhibitory effect on the growth of cancer cells (References 6-8). Potential mechanisms for crocetin mediated inhibition of tumor growth include the reduction in the synthesis of DNA, RNA and protein (References 21-22). It has also been demonstrated that crocetin inhibits RNA polymerase II activity (References 8 and 13). Crocetin also interferes with histon H1 structure and H1-DNA interactions suggesting for another possible mechanism of anticarcinogenic action (Reference 15). The exact mechanism of the protective activity of crocetin is not clear at present, but several hypotheses have been advanced, which suggest that carotenoids can convert to vitamin A, can enhance carcinogen metabolism, can act as an antioxidant, or can inhibit nucleic acid synthesis (References 7-8).

In the present study, we separated novel crocetin compounds using HPLC and LC/MS. In particular, five fractions were separated from the commercial crocetin, of which the 5$^{th}$ fraction showed most effective inhibition of proliferation and apoptosis. Similarly, pancreatic cancer growth in nude mice was also significantly inhibited due to the oral administration with crocetinic acid. Therefore, it was imperative to investigate the effect of novel crocetinic acid on the proliferation of pancreatic cancer cells and pancreatic tumor regression in nude mice.

Purified #5 fraction demonstrated most pronounced effect on proliferation and apoptosis even at 1-10 mM concentration and showed higher potency than commercial crocetin. Crocetinic acid also significantly inhibited proliferation both BxPc3 and Panc-1 cells and stimulated apoptosis in those cell lines comparison to commercial crocetin. This indicated that purified #5 fraction is most potent and LS/MS and NMR suggested this compound as crocetinic acid. Due to the higher potency of Fraction #5 as crocetinic acid, most of the work continued only with crocetinic acid.

EGFR is another critical regulator of cellular proliferation and differentiation and plays a central role in tumor proliferation and growth (References 24-26). Crocetinic acid significantly reduces EGFR expression and phosphorylation as indicated by the ratio in pancreatic cancer cells. Immunohistochemical and western blot analysis revealed that a significant decrease of EGFR phosphorylation and expression in the tumors, which developed in nude mice after crocetin treatment. These studies indicated that crocetin is a very effective inhibitor of EGFR activity and that inhibition correlates with impaired growth.

Crocetinic acid showed cytotoxicity to tumor cells (References 7-8). Therefore, it is plausible that it stimulated apoptosis or programmed cell death. Bcl-2, an antiapoptotic protein can be used to measure levels of tissue apoptotic cell death. Bcl-2 protein is known to inhibit apoptosis induced by a variety of physiological and pathological stimuli (References 27-28). Bax has a proapoptotic effect and also counters anti-apoptotic effect of Bcl-2 (References 27-28). It has been proposed that the ratio of Bax/Bcl-2 may govern the sensitivity of cells of apoptotic stimuli (References 29-30). In this study, the ratio of Bax/Bcl-2 was significantly increased in both pancreatic cancer cells as well as in pancreatic tumors after crocetin treatment, which suggested that the reduction on imbalance between antiapoptotic (Bcl-2) and proapoptotic (Bax) could be a major factor in antitumorigenic activity of crocetin.

It is now widely believed that long-lived, uncommon cells are tissue stem cells (SCs) or cells derived from them that acquire the ability to self-renew. Self-renewal, one of the defining characteristics of stem cells, is a cell division in which one or both of the resulting daughter cells remain undifferentiated, retaining the ability to give rise to another stem cell with the same capacity to proliferate as the parental cell (References 31-32). A hallmark feature of cancer stem cells (CSC) is the formation of large, floating spheres, termed mammospheres, that can be serially passaged (Reference 33). These spheres are highly tumorigenic and capable of forming colonies in vitro. The CSC theory asserts that many types of cancer are initiated from and maintained by a minor population of tumorigenic cells that are capable of continuous self-renewal and differentiation (References 34-35). This cell population undergoes unlimited proliferation and gives rise to differentiated cells, developing new tumors phenotypically recapitulating the original tumors (Reference 36).

On the basis of those observations, we have developed pancospheres markers for self-renewal of CSC and which when treated with HPLC purified different fractions and #5 fractions, showed significant inhibition of spheroid formation. This observation indicated that crocetinic acid inhibited CSC derived from cancer cells and suggested that crocetinic acid impaired self-renewal of CSC.

Further, we have demonstrated that Doublecortin and Ca$^{2+}$/calmodulin-dependent kinase-like-1 (DCLK-1) was significantly inhibited after crocetinic acid treatment. DCLK-1 has been shown to be a novel putative stem/progenitor marker that can be used to isolate normal pancreatic stem/progenitors, and potentially regenerates pancreatic tissues (References 37-38).

Next, we measured hedgehog signaling pathways, which are involved in self-renewal of CSC. Hedgehog-Gli signaling has also been shown to control the self-renewal behavior of human glioma CSCs and tumorigenicity (Reference 18). Hedgehog signals through binding to its transmembrane receptor Patched (Ptch). In the absence of hedgehog ligands (Sonic Hedgehog), Ptch associates with Smoothened (Smo) and blocks Smo function (References 18, 35, and 39). Crocetinic acid (Fraction #5) inhibited smoothed and released patched which showed increased expression due to treatment. When hedgehog binds to Ptch, Smo is released, triggering dissociation of transcription factors, Gli1 and suppressor of Fused (SuFu), leading to transcription of an array of genes, such as cyclin D1 (References 18, 35, and 39). Crocetinic acid inhibited smoothened, SUFU, Gli1 and cyclinD1 that suggested inhibition of Hegdgehog-Gli signaling pathways and self-renewal of CSC.

As suggested by our observations on the inhibition of proliferation and growth due to treatment of crocetinic acid both in vitro and in vivo, the potential utility of crocetin is very much similar in both in vitro and in vivo. The dosages of crocetin used in vitro and in vivo studies are also comparable as suggested by other investigators (References 4, 7, 8, and 23). It is also noteworthy that crocetinic acid was used in vivo longer periods of time in this study, whereas it was used in vitro until 72 hours. Another major problem in the use of anticancer agents is their toxic effect on normal cells. The concentrations of crocetinic acid used in both in vitro and in vivo study are relatively nontoxic to human cells (References 2, 3, 4, 7, and 8). It was reported previously the $LD_{50}$ of crocetin is very high 2 g/kg (References 2, 3, 7, and 8). It has also been suggested that carotenoids are well tolerated at high doses and numerous studies have supported their use in cancer chemoprevention and chemotherapy (References 2 and 5). Crocetinic acid could be relatively non-toxic with a potential for an antitumor effect.

In summary, our present study demonstrated that crocetin down-regulated growth and proliferation stimulated apoptosis and resulted in significant growth regression in in vivo pancreatic tumors. At present, it is not known that the effect of crocetinic acid on pancreatic cancer regression is its own receptor dependent or independent mechanisms, which will be investigated in future to understand exact mechanism of crocetin action.

In conclusion, this study indicated for the first time that crocetin could be used as a novel therapy for pancreatic cancer due to significant antitumorigenic effect, and thereby can be of great therapeutic benefit in future.

The invention also provides pharmaceutical or dietary supplemental compositions comprising crocetinic acid. Accordingly, the compound crocetinic acid, can be formulated for oral or parenteral administration for the therapeutic or prophylactic treatment of diseases or conditions associated with various forms of cancer, and specifically pancreatic cancer.

By way of illustration, the compound can be admixed with conventional pharmaceutical carriers and/or excipients and used in the form of tablets, capsules, elixirs, suspensions, syrups, wafers, and the like. Such pharmaceutical compositions contain from about 0.1 to about 90% by weight of the active compound crocetinic acid, and more specifically from about 5 to about 30%. The pharmaceutical compositions may contain common carriers and excipients, such as corn starch, gelatin, lactose, sucrose, microcrystalline cellulose, kaolin, mannitol, dicalcium phosphate, sodium chloride, and alginic acid. Disintegrators commonly used in the formulations of this invention include croscarmellose, microcrystalline cellulose, corn starch, sodium starch glycolate and alginic acid.

A liquid composition will generally consist of a suspension or solution of the compound or pharmaceutically acceptable salt in a suitable liquid carrier(s), for example ethanol, glycerine, sorbitol, non-aqueous solvent such as polyethylene glycol, oils or water, optionally with a suspending agent, a solubilizing agent (such as a cyclodextrin), preservative, surfactant, wetting agent, flavoring or coloring agent.

Alternatively, a liquid formulation can be prepared from a reconstitutable powder. For example a powder containing active compound, suspending agent, sucrose and a sweetener can be reconstituted with water to form a suspension; and a syrup can be prepared from a powder containing active ingredient, sucrose and a sweetener.

A composition in the form of a tablet can be prepared using any suitable pharmaceutical carrier(s) routinely used for preparing solid compositions. Examples of such carriers include magnesium stearate, starch, lactose, sucrose, microcrystalline cellulose and binders, for example polyvinylpyrrolidone. The tablet can also be provided with a color film coating, or color included as part of the carrier(s). In addition, active compound can be formulated in a controlled release dosage form as a tablet comprising a hydrophilic or hydrophobic matrix.

A composition in the form of a capsule can be prepared using routine encapsulation procedures, for example by incorporation of active compound and excipients into a hard gelatin capsule. Alternatively, a semi-solid matrix of active compound and high molecular weight polyethylene glycol can be prepared and filled into a hard gelatin capsule; or a solution of active compound in polyethylene glycol or a suspension in edible oil, for example liquid paraffin or fractionated coconut oil can be prepared and filled into a soft gelatin capsule.

Tablet binders that can be included are acacia, methylcellulose, sodium carboxymethylcellulose, poly-vinylpyrrolidone (Povidone), hydroxypropyl methylcellulose, sucrose, starch and ethylcellulose. Lubricants that can be used include magnesium stearate or other metallic stearates, stearic acid, silicone fluid, talc, waxes, oils and colloidal silica.

Flavoring agents such as peppermint, oil of wintergreen, cherry flavoring or the like can also be used. Additionally, it may be desirable to add a coloring agent to make the dosage form more attractive in appearance or to help identify the product.

The compounds of the invention and its pharmaceutically acceptable salts that are active when given parenterally can be formulated for intramuscular, intrathecal, or intravenous administration. A typical composition for intramuscular or intrathecal administration would consist of a suspension or solution of active ingredient in an oil, for example arachis oil or sesame oil. A typical composition for intravenous or intrathecal administration would consist of a sterile isotonic aqueous solution containing, for example active ingredient and dextrose or sodium chloride, or a mixture of dextrose and sodium chloride. Other examples of aqueous solution include lactated Ringers injection, lactated Ringer's plus dextrose injection, Normosol-M and dextrose, Isolyte E, acylated Ringer's injection, and the like. Optionally, a co-solvent, for example, polyethylene glycol; a chelating agent, for example, ethylenediamine tetracetic acid; a solubilizing agent, for example, a cyclodextrin; and an antioxidant, for example, sodium metabisulphite, may be included in the formulation. Alternatively, the solution can be freeze-dried and then reconstituted with a suitable solvent just prior to administration.

The compound of the invention which is active on rectal administration can be formulated as suppositories. A typical suppository formulation will generally consist of active ingredient with a binding and/or lubricating agent such as a gelatin or cocoa butter or other low melting vegetable or synthetic wax or fat.

The active compound would be effective over a wide dosage range and is generally administered in a therapeutically effective amount. It, will be understood, however, that the amount of the compound actually administered will be determined by a physician, in light of the relevant circumstances, including the condition to be treated, the chosen route of administration, the actual compound administered and its relative activity, the age, weight, and response of the individual patient, the severity of the patient's symptoms, and the like. Suitable doses are selected to effect a blood concentration of about 100-300 µM, preferably 100 µM.

According to the invention, a compound can be administered in a single daily dose or in multiple doses per day. The treatment regimen may require administration over extended periods of time, for example, for several days, for from one to six weeks, or longer.

Suitable formulations for use in the present invention can be found in Remington's Pharmaceutical Sciences, Mace Publishing Company, Philadelphia, Pa., 17th ed. (1985).

While this invention has been described as having preferred sequences, ranges, steps, order of steps, materials, structures, symbols, indicia, graphics, color scheme(s), shapes, configurations, features, components, or designs, it is understood that it is capable of further modifications, uses and/or adaptations of the invention following in general the principle of the invention, and including such departures from the present disclosure as those come within the known or customary practice in the art to which the invention pertains, and as may be applied to the central features hereinbefore set forth, and fall within the scope of the invention and of the limits of the claims appended hereto or presented later. The invention, therefore, is not limited to the preferred embodiment(s) shown/described herein.

REFERENCES

The following references, and those cited in the disclosure herein, are hereby incorporated herein in their entirety by reference.

1. Siegel, R., Naishadham, D. and Jemal, A. Cancer Statistics 2013, CA Cancer J. Clin 63, 11-30, 2013.
2. Nair S C, Panikkar B, Panikkar K R. Antitumor activity of saffron (*Crocus sativus*). Cancer Lett 1991; 57:109-14.
3. Abdullaev F I, Frenkel G D. Effect of saffron on cell colony formation and cellular nucleic acid and protein synthesis. Biofactors 1992; 3:201-04.
4. Abdullaev F I. Cancer chemopreventive and tumoricidal proporties of saffron (*Crocus sativus* L.) Exp. Biol. Med. 2002; 227:20-5.
5. Abdullaev F I, Espinosa-Aguirre J J. Biomedical properties of Saffron and its potential use in cancer therapy and chemoprevention trials. Cancer Detection and Prevention. 2004; 28, 426-32.
6. Tarantilis P A, Morjani H, Polissiou M, et al. Inhibition of growth and induction of differentiation of promyelocytic leukemia (HL-60) by carotenoids from *C. Sativus* L. Anticancer Res 1994; 14:1913-18.
7. Dhar, A.; Mehta, S.; Dhar, G., Dhar, K.; Banerjee, S.; Van Veldhuizen, P.; Campbell, D. R.; Banerjee, S. K. Crocetin inhibits pancreatic cancer cell proliferation and tumor progression in a xenograft mice model. *Mol. Cancer Ther.*, 2009, 8, 315-323.
8. Gutheil, W., Reed, G., Ray, A., Anant, S. and Dhar, A. Crocetin: a novel agent derived from saffron for prevention and therapy for cancer. Current Pharmaceutical Biotechnology 13, 173-179, 2012.
9. Giaccio, M. Crocetin from Saffron: An active component of an ancient spice. *Clin. Rev. Food Sc. Nutr.,* 2004, 44, 155-172.
10. Sujata, V.; Ravishankar, G. A.; Venkataramn, L. V. Methods for the analysis of the saffron metabolites crocin, crocetins, picocrocin and safranal for the determination of the quality of the spice using thin layer chromatography, high performance liquid chromatography and gas chromatography. *J. Chromatogr.,* 1992, 624, 497-502.
11. Li, N.; Lin, G.; Kwan, Y-W.; Min, Z-D. Simultaneous quantification of five major biologically active ingredients of saffron by highperformance liquid chromatography. *J. Chromatogr.,* 1999, 849, 349-355.
12. Abdullaev F I. Inhibitory effect of Crocetin on intracellular nucleic acid and protein synthesis in malignant cells. Toxicol Lett 1994; 70:243-51.
13. Nair S C, Kururumboor S K, Hasegawa J H Saffron chemoprevention in biology and medicine: a review. Cancer Biother 1995; 10:257-64.
14. Asrafi M, Bathari S Z, Taghikhani M, et al. The effect of carotenoids obtained from saffron from on histone H1 structure and H1-DNA interaction. Int J Biol Macromol 2005; 36:246-52.
15. Magesh, V.; Singh, J. P.; Selvendiran, K.; Ekambaram, B.; Sakthisekaran, D. Antitumor activity of crocetin in accordance to tumor incidence, antioxidant status, drug metabolizing enzymes and histopathological studies. *Mol. Cell. Biochem.,* 2006, 287, 127-135.
16. Chrissanthi D G, Lamar F N, latrou G, et al. Inhibition of breast cancer cell proliferation by style constituents of different *Crocus* species. Anticancer Res 2007; 27, 357-62.
17. Dhar, A., Fogt, L., Subramaniam, D. and Anant, S. Cancer Stem Cells Novel target using dietary components for prevention and treatment. "Nutraceutical and Cancer ed Sarkar, F. S. P11-38, 2012.
18. Rosenberg L, Lipsett M. Biotherapeutic approaches to pancreatic cancer. Expert Opin Biol Ther 2003; 3: 319-37.
19. Rosenberg L, Lipsett M. Biotherapeutic approaches to pancreatic cancer. Expert Opin Biol Ther 2003; 3: 319-37.
20. Balasubramonian S, Chandraratna R A, Eckert, R L. A novel-retenoid related molecule inhibits pancreatic cell proliferation be a retinoid receptor independent mechanism via suppression of cell cycle regulatory protein function and induction of caspase-associated apoptosis. Oncogene 2005; 24:4257-70.
21. Nair S C, Kururumboor S K, Hasegawa J H Saffron chemoprevention in biology and medicine: a review. Cancer Biother 1995; 10:257-64.
22. Mathews-Roth M M. Effect of crocetin on experimental skin tumors. Oncology 1982; 39, 362-64.
23. Lemoine N R, Hughes C M, Barton, C. M, et al. The epidermal growth factor receptor in human pancreatic cancer. J Pathol 2002; 166: 7-12.
24. Dhar A, Mehta S, Banerjee S, et al. Epidermal growth factor receptor, Is a novel therapeutic target for pancreatic cancer? Front Biosci 2005; 10:1763-67.
25. Yamanka Y, Freiss H, Korbin M S, et al. Coexpression of epidermal growth factor receptor and ligands in human pancreatic cancer associated with enhanced tumor aggressiveness. Anticancer Res 1993; 13:565-69.
26. Tsujimoto Y. Stress resistance conferred by high level of bcl-2 protein in human lyphoblastoid cell. Oncogene 1989; 4:1331-39.
27. Hawkins C J, Vaux, D. Analysis of the role of bcl-2 in apoptosis. Immunol Rev 1994; 142: 127-39
28. Oltvai Z N, Milliman C L, Korsmeyer S J. Bcl-2 hetrodimerizes in vivo with a conserved homolog, Bax, that acclerates program cell death. Cell 1993; 74: 609-19.
29. Yin X M, Oltvai, Z N, Korsmeyer S J. BH1 and Bh2 domains of Bcl-2 are required for inhibition of apoptosis and hetrodimerization with Bax. Nature 1994; 369: 321-23.
30. Lapidot, T, Sirard, Sirard, C, Vormoor, J et al (1994) A cell initiating human acute myeloid leukemia after transplantation into SCID mice. Nature 367; 645-648.
31. Bonnet D, Dick J E. (1997) Human acute myeloid leukemia is organized as a hierarchy that originates from a primitive hematopoietic cell. Nat Med 3, 730-737.
32. Gupta, S, Hussain, T, Mukhtar, H (2003) Molecular pathway for (−)-epigallocatechin-3-gallate-induced cell cycle arrest and apoptosis of human prostate carcinoma cells. Arch Biochem Biophys 410, 177-185.
33. Korkaya H, Paulson A, Charafe-Jauffret E, et al (2009).
34. Regulation of mammary stem/progenitor cells by PTEN/Akt/beta-catenin signaling. PLoS Biol e1000121, 7.
35. Liu S, Dontu G, Wicha M S (2005) Mammary stem cells, self-renewal pathways, and carcinogenesis. Breast Cancer Res 7, 86-95.
36. Zhou B B, Zhang H, Damelin M et al (2009) Tumour-initiating cells: challenges and opportunities for anticancer drug discovery. Nat Rev Drug Discov. 8, 806-823.
37. Mwangi, S M, Srinivasan, S (2010) DCAMKL-1: A new horizon for pancreatic progenitor identification (Comment). Am J Physioi Gastrointest Liver Physiol 299, G303-G310.
38. May, F R, Sureban, S M, Lightfoot, S A et al (2010) Identification of a novel putativelpancreatic stem cell marker DCAMKL-1 in normal mouse pancreas. Am J Physiol Gastrointest Liver Physiol 299, G303-G310,
39. Cohen Jr M M. (2003) The hedgehog signaling network. Am J Med Genet 123A, 5-28.
40. Jemal, A., Siegel, R., Ward, E., Hao, Y., Xu, J. and Thun, M. J. Cancer Statistics, 2009. CA Cancer J. Clin 59, 225-249, 2009.
41. Chua, Y. J. and Zalcberg, J. R. Pancreatic Cancer—is the wall crumbling? Annals of Oncology 19, 1224-1230, 2008.

What is claimed is:
1. An in vivo method of impairing self-renewal of cancer stem cells, comprising:
   a) providing a predetermined amount of cancer stem cells;
   b) subjecting the cancer stem cells to an effective amount of a compound, composition, or a formulation comprising crocetinic acid in an amount between and including 0.5 mg/kg body weight and 4 mg/kg body weight; and c) comparing the level of Sonic Hedgehog signaling in the cancer stem cells before and after the step b) so as to inhibit the expression of the Sonic Hedgehog signaling.
2. The method of claim 1, wherein:
   a) the cancer stem cells comprise pancreatic stem cells.

* * * * *